(12) United States Patent
Sawyer

(10) Patent No.: US 6,403,063 B1
(45) Date of Patent: Jun. 11, 2002

(54) METHOD OF TREATING NAIL FUNGUS

(76) Inventor: Kenneth I. Sawyer, 43 Harbor Dr., Stamford, CT (US) 06902

( * ) Notice: Subject to any disclaimer, the term of this patent is extended or adjusted under 35 U.S.C. 154(b) by 0 days.

(21) Appl. No.: 09/626,336

(22) Filed: Jul. 26, 2000

Related U.S. Application Data

(60) Provisional application No. 60/145,603, filed on Jul. 26, 1999.

(51) Int. Cl.$^7$ .............................. A61K 6/00; A61K 7/00; A61K 7/04
(52) U.S. Cl. ........................................ 424/61; 424/401
(58) Field of Search .................................. 424/61, 401

(56) References Cited

U.S. PATENT DOCUMENTS

| | | | |
|---|---|---|---|
| 2,683,730 A | 7/1954 | Seeger et al. ............... 260/453 |
| 2,759,903 A | 8/1956 | Epstein et al. .............. 260/29.3 |
| 3,004,896 A | 10/1961 | Heller et al. ................... 167/90 |
| 3,189,615 A | 6/1965 | Heller et al. ................. 260/308 |
| 3,349,000 A | 10/1967 | Joos ............................ 167/85 |
| 3,349,164 A | 10/1967 | McCellan et al. .......... 260/453 |
| 4,058,442 A | 11/1977 | Lee, Jr. et al. .......... 204/159.12 |
| 4,328,322 A | 5/1982 | Baron ......................... 521/163 |
| 4,560,555 A | 12/1985 | Snider ......................... 424/78 |
| 5,039,775 A | * 8/1991 | Oyaizu ........................ 528/68 |
| 5,162,037 A | 11/1992 | Whitson-Fischman ....... 600/12 |
| 5,192,536 A | 3/1993 | Huprich ................... 424/78.08 |
| 5,264,206 A | 11/1993 | Bohn et al. .................... 424/61 |
| 5,319,058 A | 6/1994 | Hattori et al. ................. 528/67 |
| 5,346,692 A | 9/1994 | Wohlrab ....................... 424/61 |
| 5,391,367 A | 2/1995 | De Vincentis et al. ........ 424/61 |
| 5,464,610 A | 11/1995 | Haynes et al. ................ 424/61 |
| 5,487,776 A | 1/1996 | Nimni ...................... 106/18.35 |
| 5,516,873 A | 5/1996 | Hicks et al. ................... 528/60 |
| 5,650,159 A | 7/1997 | Lion et al. ................... 424/401 |
| 5,652,256 A | 7/1997 | Knowles ..................... 514/399 |
| 5,679,648 A | 10/1997 | McCaffrey et al. ............ 514/46 |
| 5,696,105 A | 12/1997 | Hackler ....................... 514/172 |
| 5,696,164 A | 12/1997 | Sun et al. .................... 514/562 |
| 5,733,538 A | 3/1998 | Riffle ....................... 424/78.08 |
| 5,830,442 A | 11/1998 | Beaver ......................... 424/61 |
| 5,840,283 A | 11/1998 | Sorenson et al. ............. 424/61 |
| 5,866,105 A | 2/1999 | Richter et al. ................ 424/61 |
| 5,889,039 A | 3/1999 | Knowles ..................... 514/399 |

FOREIGN PATENT DOCUMENTS

EP      0 630 666      11/1998

* cited by examiner

*Primary Examiner*—Thurman K. Page
*Assistant Examiner*—S. Howard
(74) *Attorney, Agent, or Firm*—Frommer Lawrence & Haug LLP

(57) ABSTRACT

A method of treating nail fungus is disclosed. The method comprises applying a therapeutic polyurea composition to an affected nail. Such nail composition is selected from a reaction solution, a stabilized reaction solution, a blocked reaction solution or a mixture of any of the foregoing solutions.

41 Claims, No Drawings

METHOD OF TREATING NAIL FUNGUS

This applications claims priority from U.S. provisional application Serial No. 60/145,603 filed Jul. 26, 1999, which is incorporated herein by reference.

BACKGROUND OF THE INVENTION

1. Field of the Invention

This invention relates to a method of treating nail fungus and more particularly to a method of utilizing a therapeutic polyurea composition by topical administration thereof to the affected nail.

2. Description of the Prior Art

Humans and animals alike are commonly plagued by the infiltration of micro-organisms beneath the nail, claw or hoof which result in a disease condition causing pain, discoloration, and frequently loss of the unguis. In humans, for example, some diseases which attack the nail or nail bed can be treated fairly successfully with the use of cleansing and/or antiseptic preparations, while other diseases require treatment by such means as systemic drug therapy. Nonetheless, many disease conditions of the nail, particularly onychomycosis (i.e., fungal diseases), have had a relatively low success rate for treatment due to the intransigent nature of the infectious micro-organisms.

It has been estimated that greater than twenty percent (20%) of the population of the United States over the age of 40 suffers from onychomycosis of the fingernails or toenails. The disease is known to occur to a lesser extent in people below the age of forty, but the occurrence of disease is still significant. Unfortunately, the current modalities for treatment of onychomycosis show a very low success rate.

Mycoses of the nails (onychomycoses) are intractable types of disease which have hitherto not been possible to treat satisfactorily. The term onychomycoses embraces various types of mycoses of the nails, of which those caused by dermatophytes are the most difficult to treat, whereas the mycoses of the nails caused by yeast-like fungi have hitherto been those which it has been possible most readily to treat successfully.

The difficulty with onychomycoses caused by dematophytes is additionally that they make a considerable contribution to the spread of infectious fungi. Various routes have been followed hitherto for their treatment, but without permanent success.

Common means of treating microbial diseases, including onychomycosis, include oral administration of drugs and laser therapy. Laser therapy, as yet, is not well-developed nor widely practiced, and is very expensive because it must be conducted in a doctor's office by a trained technician. Systematic drug therapy through oral administration has also proven to be relatively unsuccessful because of drug intolerances, the expense of the medications and low patient compliance. Typically, systemic oral treatment with antifungal agents requires long term treatment with a potential for toxic side effects.

A common means of treating onychomycosis is to remove the nail completely and topically apply medication to the underlying nail bed. However, not only is such treatment cosmetically unsightly, but the fungus which invades the nail often remains in the matrix of the finger or toe (where the nail is formed) and the disease reoccurs immediately upon, or during ingrowth of the new nail. Moreover, because of the aggressive nature of this treatment, the regrown nails are often deformed in shape.

A conservative method comprises topical treatment of the nails with specific substances having antimycotic activity. A very wide variety of treatment methods has been tried for this. Thus, in a combined treatment, the nails have initially been treated with solutions of the substances having antimycotic activity, and cream dressings have been applied each night. This treatment method is by its nature also very unpleasant for, and a psychological strain on, the patient. On the one hand, the nails have to be treated with a solution several times a day. On the other hand they have to be provided with dressings, particularly at night. Furthermore, it is necessary for the diseased nails to be filed or scraped down continually, which not only is troublesome but also contributes to spreading the pathogens. The results of all this are that many of the patients do not persist with the treatment, which usually takes several months; on the contrary, they become discouraged and negligent, and thus the therapy is unsuccessful. Also detrimental to the success of treatment by this method is that the solutions and creams are usually miscible with water or hydrophilic and thus can be removed again from the surface of the nail or dissolved out of the nail on washing, bathing and showering, and thus may need to be reapplied thereafter.

Undoubtedly, treatment of diseases involving nails would be greatly enhanced by the ability to access the area around and below the nail, as well as to penetrate the nail itself, without having to remove the nail. However, the thick and/or hardened nature of nails renders access through, and to the areas below, the nail very difficult. The same can be said of diseases involving the claws or hooves of animals.

The usefulness of antifungal drugs in treating onychomycosis has been limited heretofore because of resistance to penetration of the nail or because of limited access to the nail bed through the nail. Thus, it would be an improvement in the art to provide means for enhancing penetration of the nail so that treatment of the nail with medication may occur at the situs and without having to remove or otherwise significantly damage the nail. It would also be advantageous to provide such penetration means at a reasonable cost to the consumer, and in a form which would facilitate and encourage proper and consistent self-use by the afflicted person.

SUMMARY OF THE INVENTION

This invention relates to a method of treating a nail fungus and, more particularly, to a method utilizing a therapeutic polyurea composition by topical administration thereof to the affected nail.

The method comprises applying a therapeutic polyurea composition selected from (a) a reaction mixture comprising a first component of an oligomeric amino benzoic acid ester or amide having the formula

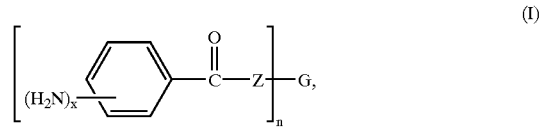

where n is an integer from 2 to 4; each x is one or two; each benzoyl nucleus is para, meta, or di meta amino-substituted; each Z is —O— or —N—; and G is an n-valent radical obtained by removal of hydroxy groups or amino groups from an n-valent polyol or polyamine having a molecular weight of from about 400 to about 6,000; and a second component comprising a polyisocyanate; (b) a stabilized reaction mixture comprising the first component of the oligomeric amino benzoic acid ester or amide of formula I, combined with the second component of the polyisocyanate in a stabilizing carrier; (c) a blocked reaction mixture, comprising the first component of formula I having at least one of its aromatic amino groups blocked by a reaction with an aldehyde, combined with the second component, polyisocyanate; and (d) a mixture of any the foregoing.

DETAILED DESCRIPTION

A suitable first component is selected from among an oligomeric amino benzoic acid ester or amide and an aromatic diamine derivative. The oligomeric amino benzoic acid ester or amide has the formula,

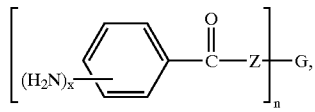
(I)

wherein n is an integer of from 2 to 4, each x is one or two; each benzoyl nucleus is para-, meta- or di-meta amino substituted; each Z is

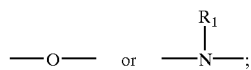

and G is an n-valent radical obtained by the removal of hydroxyl groups or amino groups, respectively, from an n-valent polyol or polyamine having a molecular weight of from about 400 to about 6,000. It will be appreciated that the characterization of radical G (as an n-valent radical which may be obtained by the removal of hydroxyl groups or amino groups, respectively, from an n-valent polyol or polyamine) is set forth for convenience in defining the nature of radical G per se, notwithstanding that abstraction or removal of hydroxyl or amino groups from such polyol or polyamine is not mechanistically involved in the synthesis or production of the oligomeric aminobenzoic acid esters and amides thereof; and $R_1$ is hydrogen $C_1$–$C_{20}$alkyl, [($C_1$–$C_{20}$ alkoxy)aryl]methyl or [C1–C20 alkyl)aryl]methyl.

It will be seen from inspection of the formula I set forth hereinbefore that the oligomeric aminobenzoic acid esters utilized in the present invention comprise di-, tri- and tetra-(aminobenzoate) esters of oligomeric polyol materials where n is, respectively, 2, 3 or 4. Correspondingly, oligomeric aminobenzoic acid amides comprise di, tri- and tetra-(aminobenzoic acid) amides of oligomeric polyamine materials where n is respectively 2, 3, or 4. Inasmuch as the aromatic rings of the benzoyl moieties of the esters and amides each contain one or two amino groups, the oligomeric amino benzoic acid esters and amides may be termed oligomeric polyamines. Accordingly, the term "oligomeric polyamine" can be utilized in reference to the essential aminobenzoic acid ester or amide components of the polyaddition product and process of the present invention.

The oligomeric aminobenzoic acid esters utilized in the practice of the polyaddition process of the present invention are aminobenzoate esters of oligomeric polyol materials and can be conveniently provided by reaction of a nitro-substituted benzoyl halide, or a nitro-substituted benzoic acid, with a suitable polyol, such as polyalkylene ether or ester polyol, followed by reduction of the nitro groups of the resulting product to the corresponding amino groups. Thus, for example, an oligomeric di-(p-aminobenzoate) ester useful herein can be prepared by reaction of two moles of p-nitrobenzoyl chloride with one mole of a dihydric alcohol such as poly(ethylene glycol) having a molecular weight in the range of from about 400 to about 6,000 and by reduction of the resulting poly(ethylene glycol) di(p-nitrobenzoate) etc.

In like manner, oligomeric aminobenzoic acid amides useful herein can be provided by reaction of a nitro-substituted benzoyl halide, or a nitro-substituted benzoic acid, with a suitable polyamine, followed by a reduction of the benzoyl halide or benzoic acid nitro-substitutes to corresponding amino groups. For example, an oligomeric di(p-aminobenzoic acid) amide useful herein can be prepared by reaction of two moles of p-nitrobenzoic acid with one mole of an oligomeric diamine such as propoxlated propylene diamine having a molecular weight in the range of from about 400 to 6,000 and by reduction of the nitro groups to amino groups.

The nature of radical G of the aminobenzoic acid esters and amides can vary and will depend upon the nature of the oligomeric polyol and polyamine materials utilized in the preparation thereof. As indicated previously, the radical G will be derived from a polyol or polyamine material having a molecular weight of from about 400 to about 6,000. Preferably, the polyol or polyamine will have a molecular weight in the range of about 650 to 2,000. The radical G can comprise an n-valent saturated or unsaturated, straight chain or branched chain hydrocarbon radical which can be interrupted by oxygen ether atoms. For example, where a polyether polyol or a polyether polyamine is utilized in the preparation of an oligomeric aminobenzoic acid or amide, the corresponding G radical will comprise repeating oxygen ether atoms. Preferably, radical G will include such oxygen ether atoms.

It will be appreciated from inspection of the hereinbefore described representative formula I that the nature of n-valent radical G will vary with the value of integer n. Thus, where n is two, radical G will be a divalent radical —G— obtained by removal or abstraction of two hydroxyl or amino groups, respectively, from an oligomeric polyol or polyamine having a molecular weight of from about 400 to about 6,000. In the case where n is three, G will represent a trivalent radical

obtained by removal of three hydroxyl or amino groups from a polyol or polyamine having a molecular weight in the same range. Similarly, when n is four, radical G will represent a tetravalent radical.

obtained by removal of four hydroxyl or amino groups from a polyol or polyamine having a molecular weight in the same range.

The Z moieties of the oligomeric aminobenzoic acid ester and amide compounds hereof can independently be oxygen or imino groups and, accordingly, each Z is defined as being

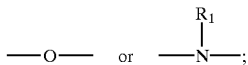

While the utilization of, for example, an oligomeric polyol or polyamine having, respectively, only hydroxyl or amino group will be preferred from the standpoint of convenience and ease of preparation, compounds having both hydroxyl and amino groups can be utilized for the preparation of mixed aminobenzoic acid ester/amide compounds hereof.

A number of polyol materials can be suitably employed for the preparation of the oligomeric aminobenzoic acid esters utilized herein. Examples of such polyols, which provide divalent, trivalent or tetravalent G radicals include oligomeric diols, such as polyalkyleneether glycols and polyalkylene-arylene-ether glycols; oligomeric triols, such as the polyalkyleneether glycerols or mixed polyalkyene-arylene-ether glycerols; and oligomeric tetrols, such as the polyalkylene ether pentaerythriols or mixed polyalkylene-arylene-ester pentaerythritols.

A preferred class of polyol materials useful in the preparation of the aminobenzoic acid esters herein comprises the polyalkyleneether glycols which provide a divalent G radical and which may be represented by the formula $HO(RO)_a$ wherein R is an alkylene radical containing up to ten carbon atoms and a is an integer sufficient to provide a molecular weight within the range of from about 400 to 6,000, and preferably, from about 650 to about 2,000. Preferably R is an alkylene radical of from 2 to 4 carbon atoms. Examples of polyalkyleneether glycols useful herein include polyethyleneether glycol, polypropylene ether glycol, polyhexyleneether glycol, polytetramethyleneether glycol, polydecamethyleneether glycol, poly-1,2-dimethyl ethyleneether glycol and the copolymer of tetrahydrofuran and 1-allyloxy-2,-3-epoxypropane. The polyalkyleneether glycols herein can be readily obtained, for example, by polymerization to suitable molecular weight of an alkylene ether, e.g., ethylene oxide, tetrahydrofuran, propylene oxide, or, an admixture thereof, in the presence of water or other low molecular weight alcohol or hydrogen-donor compound.

The polyalkylene-arylene-ether glycols can also be employed for the preparation of oligomeric p-aminobenzoic acid esters utilized herein. These glycols, similar in structure to the polyalkyleneether glycols, additionally contain arylene radicals. Thus, arylene groups such as phenylene, naphthalene and anthracene radicals can be present in the polyalkylene-arylene-ether glycols. In general, the arylene groups will be present in minor proportion relative to the alkylene groups. Normally, the glycol will contain at least one polyalkyleneether radical of molecular weight of about 500 for each arylene radical.

Another class of polyol materials suited to the preparation of oligomeric aminobenzoic acid esters useful herein comprises the class of hydroxy-containing hydrocarbon polymer materials having a molecular weight in the range of from about 400 to 6,000. Accordingly, the radical G derived therefrom will comprise an n-valent saturated or unsaturated, straight or branched chain hydrocarbon radical which may be obtained by removal of hydroxyl groups from a saturated or unsaturated straight or branched chain hydrocarbon polymer having a molecular weight within the previously set forth range. Preferably, the n-valent G radical will be an aliphatic hydrocarbon radical derived from an aliphatic hydrocarbon polyol. Examples of suitable hydrocarbon polyol materials include the polyols obtained from the polymerization of polymerizable ethylenically unsaturated monomers, such as 1,4-butadiene, and by the introduction of hydroxyl groups in known manner. Such polyol materials are known and can be prepared, for example, by free-radical initiated polymerization of a polymerizable ethylenically-unsaturated monomer to provide a dicarboxylate-substituted hydrocarbon polymer, for example, a dicarboxylate-terminated polymer. Reduction in known manner provides an aliphatic hydrocarbon polyol, for example, an aliphatic hydrocarbon diol. A suitable method for the production of such polyol materials is described in greater detail in U.S. Pat. No. 2,888,439 which is incorporated by reference hereinto in its entirety.

As indicated previously, the polyol materials useful for the preparation of the oligomeric aminobenzoic acid esters utilized herein also include polyols capable, by abstraction, respectively, of three or four hydroxyl groups, of providing a trivalent or tetravalent radical G. Thus, polyalkyleneether polyols and mixed polyalkylene-arylene-ether polyols derived from such polyhydric alcohols as glycerol, trimethylolpropane, pentaerythritol and the like can be employed. Such materials can be obtained by oxyalkylation as, for example, by reaction of glycerol or pentaerythritol with ethylene oxide, propylene oxide or a mixture thereof. The resulting trifunctional and tetrafunctional ethers may be advantageously employed for the preparation of oligomeric tri- and tetra-(aminobenzoate) esters which can be suitably employed for the production of polymers having increased cross-linking.

A variety of polyamines can be utilized for the preparation of oligomeric aminobenzoic acid amides useful herein. Examples of such polyamines, which provide divalent, trivalent or tetravalent G radicals include oligomeric diamines, triamines and tetramines. For example, oligomeric diamines useful for the provision of oligomeric aminobenzoic acid amides include polyamines of the formula

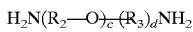

wherein each of $R_2$ and $R_3$ is a divalent saturated or unsaturated, straight chain or branched chain hydrocarbon radical; c is zero or an integer; d is an integer; and the combined value of c and d is such as to provide a molecular weight for the polyamine of from about 400 to about 6,000. Preferably, each of $R_2$ and $R_3$ is an aliphatic, straight or branched chain divalent hydrocarbon radical, e.g., an alkylene radical of from 2 to 10 carbon atoms, and more preferably from 2 to 4 carbon atoms. Suitable polyamines are known and commercially available and can be obtained, for example, by polymerization of an alkylene oxide and conversion of terminal hydroxyl groups to amino groups by known amination techniques.

The polyol and polyamine materials from which the n-valent G radical is derived can contain substituent moieties where such substituents do not interfere with the desired reaction of the aminobenzoic acid ester or amide with an isocyanate. Alkyl or halo substituents, for example, can be suitably present. The n-valent G radical can also contain repeating oxygen ether atoms as will be the case where the polyol or polyamine from which radical G is derived comprises, for example, a polyalkyleneether glycol, a polyalkyleneether glycerol, a polyalkyleneether pentaerythritol, a mixed polyalkylene-arylene-ether polyol or an amine-terminated polyalkylether. The polyol and polyamine materials can additionally contain ester linkages. Thus, polyol materials of suitable molecular weight, i.e., in the range of from about 400 to 6,000, ester linkages as may be obtained, for example, by reaction of a polycarboxylic acid and a polyhydric material can be suitably employed. An example of such a polyol having ester groups include the oligomeric polyester polyols such as may be obtained by the condensation of adipic acid and ethylene glycol.

The oligomeric aminobenzoic acid esters utilized herein for the production of polymeric products include the di-(aminobenzoate)esters(obtained, for example, by reaction of two moles of a nitro-substituted benzoyl chloride with one mole of an oligomeric glycol having a molecular weight of about 400 to about 6,000, followed by reduction of nitro-to-amino-groups); and the tri-(aminobenzoate)esters(from three moles of a nitro-substituted benzoyl chloride and one mole of an oligometric triol of molecular weight of about 400 to about 6,000, followed by reduction of nitro-to-amino-groups). Similarly, the oligomeric aminobenzoic acid esters include the tetra-(aminobenzoate) esters derived from four moles of a nitro-substituted benzoyl chloride per mole of an oligomeric tetrol of molecular weight of about 400 to about 6,000, followed by a suitable nitro-to amino group reduction. These oligomeric aminobenzoate esters can conveniently be represented by the following formulae:

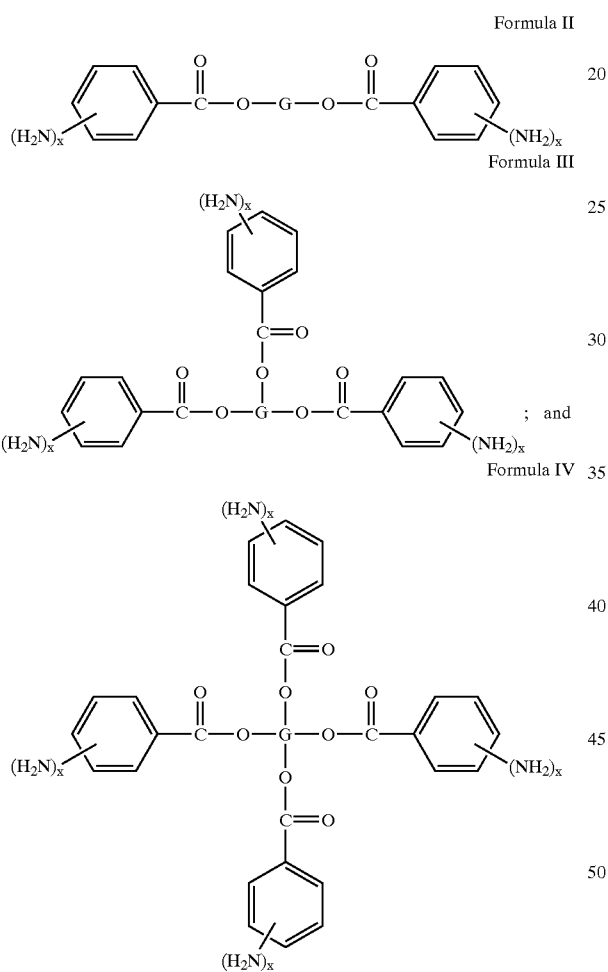

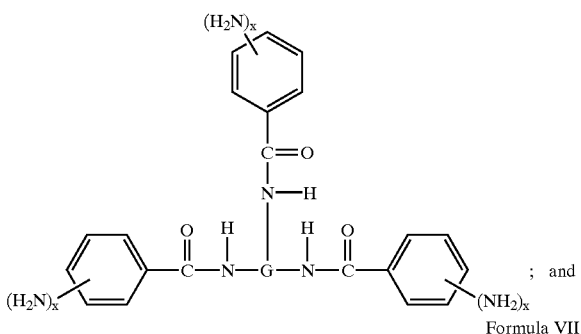

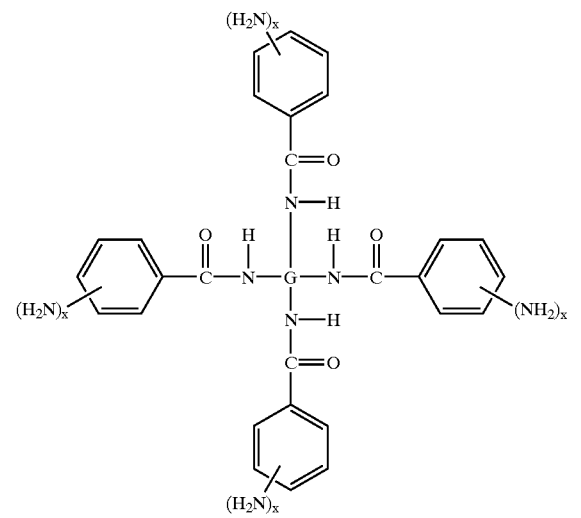

Similarly, the oligomeric aminobenzoic acid amides utilized herein for the production of polymeric products include the di-(aminobenzoic acid) amides, the tri-(aminobenzoic acid) amides and the tetra-(aminobenzoic acid) amides. These oligomeric aminobenzoic acid amides can conveniently be represented by the following formulae:

In the formulae shown for the oligomeric aminobenzoate esters hereof (Formulae II, III, and IV) and the oligomeric aminobenzoic acid amides (Formulae V, VI, and VII), G will represent, respectively, a divalent, trivalent or tetravalent radical derived from a polyol or polyamine having a molecular weight in the range of about 400 to about 6,000, and preferably, in the range of from about 650 to about 2,000. As will be apparent from inspection of each of the formulae set forth hereinbefore, the phenyl group of each benzoyl moiety contains one or two amino groups depending upon the value of each x as one or two. The amino groups are positioned such that each benzoyl nucleus is para-amino-substituted, a meta-amino-substituted or di-meta-amino-substituted. Accordingly, the oligomeric aminobenzoic acid esters and amides hereof are inclusive of para-amino-benzoic acid esters and amides, meta-aminobenzoic acid esters and amides; and di-meta-aminobenzoic acid esters. It will be appreciated that each benzoyl moiety of an oligomeric aminobenzoic acid ester or amide hereof, while para-, meta- or di-meta-amino-substituted, need not be identically substituted. Preferred oligomeric aminobenzoic acid esters and amides herein are those wherein the benzoyl moieties are each para-amino substituted. In addition to the amino-group substitution of the benzoyl moieties, the benzoyl groups can be substituted with non-interfering groups. Accordingly, the benzoyl moieties of the aminobenzoic acid ester and amide compounds hereof can be substituted with halogen, alkyl or other substituents which do not interfere with the desired polyisocyanate addition process.

Examples of oligomeric aminobenzoic acid esters useful herein and represented by Formula I include the following wherein a and b are integers having values corresponding to molecular weights polyols from which they are derived of from about 400 to about 6,000.

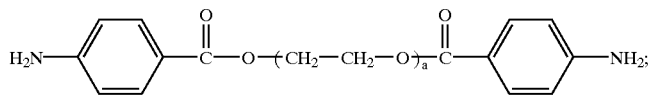

A

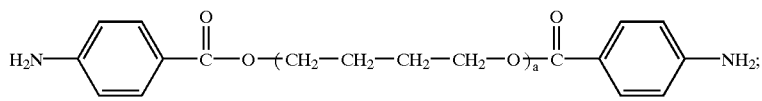

B

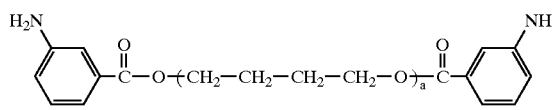

C

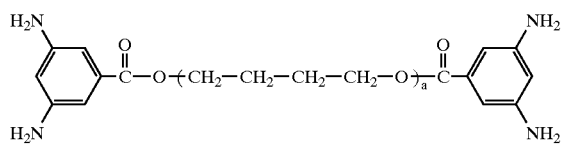

D

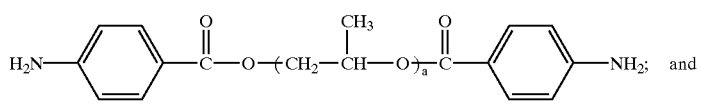

E and

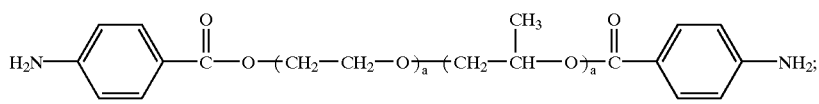

F

An example of a compound of Formula (II) B., above, is VERSALINK™ P 1000, commercially available from Air Products & Chemicals, Inc. which has the formula

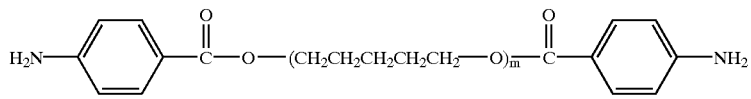

Where m=13–14, with a molecular weight of 1238.

Other commercially available products include VERSALINK™ P-650, having an average molecular weight of 830, and VERSALINK™ 250, having an average molecular weight of 485.

Examples of oligomeric aminobenzoate esters useful herein and represented by Formula III include the following wherein a and b are integers having values corresponding to the molecular weights for the polyols from which they are derived of from about 400 to about 6,000.

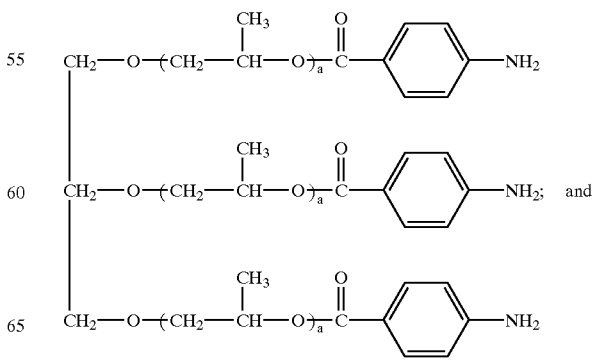

G and

-continued

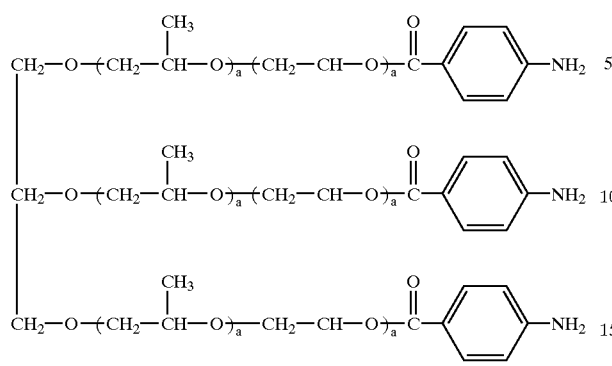

An example of an oligomeric aminobenzoate ester represented by Formula IV includes the following wherein each a is an integer having a value corresponding to a molecular weight for the polyalkyleneether pentaerythritol from which the aminobenzoate ester is derived of from about 400 to about 6,000.

An example of an oligomeric aminobenzoic acid amide useful herein and represented by Formula VI is the following wherein each c has a value corresponding to the molecular weight for the polyamine from which the amide is derived of from about 400 to about 6,000.

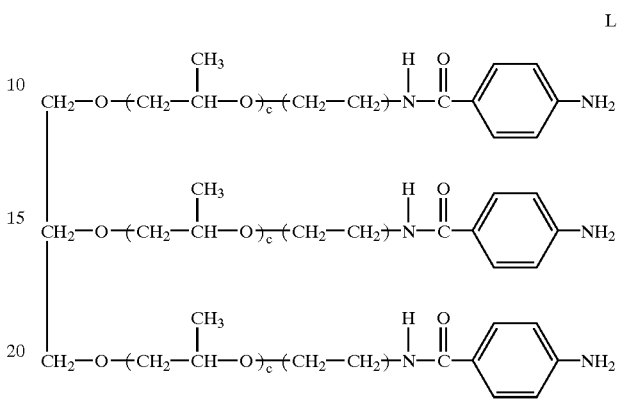

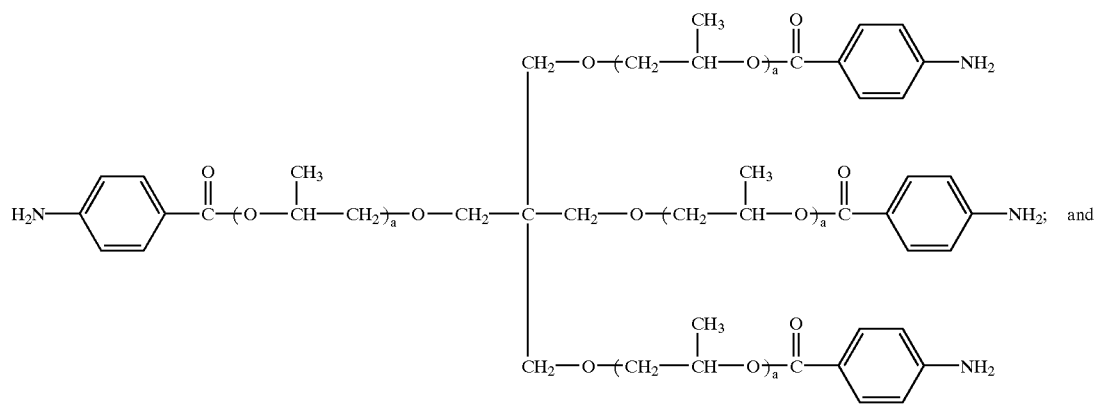

Examples of oligomeric aminobenzoic acid amides useful herein and represented by Formula V include the following wherein each c is an integer having values corresponding to molecular weights for the polyamines from which they are derived of from about 400 to about 6,000.

An example of an oligomeric aminobenzoic acid amide represented by Formula VII includes the following wherein c is an integer having a value corresponding to a molecular weight for the polyamine from which the amide is derived of from about 400 to about 6,000.

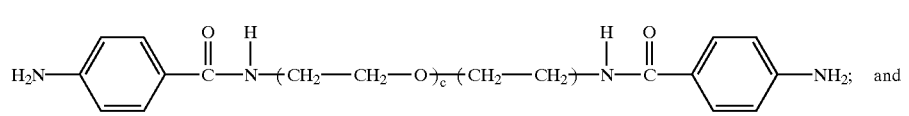

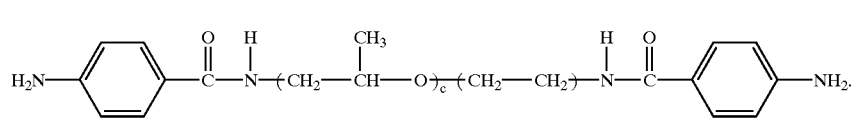

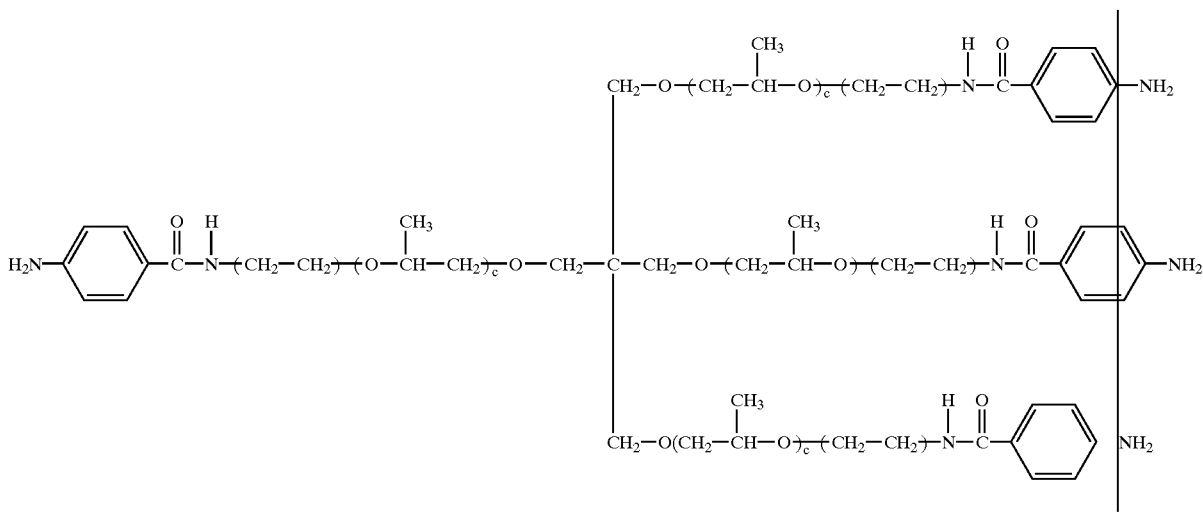

The above-described oligomeric aminobenzoic acid esters and amides and their preparation is described in U.S. Pat. Nos. 4,328,322, 5,039,775 and EP 0630666) 630666 which are incorporated by reference hereinto in their entirety for all purposes.

Examples of other aminobenzoate esters or amides include,
polyethyleneglycol bis(4-aminobenzoate);
polyethyleneglycol bis(2-aminobenzoate);
polyethyleneglycol bis(3-aminobenzoate);
polytetramethyleneglycol bis(4-aminobenzoate);
polytetramethyleneglycol bis(2-aminobenzoate);
polypropyleneglycol bis(4-aminobenzoate);
polypropyleneglycol bis(2-aminobenzoate);
poly(oxyethylene-oxypropylene)glycol bis(4-aminobenzoate);
polyoxybutyleneglycol bis(4-aminobenzoate);
polytetramethyleneglycol bis(3,5-diaminobenzoate);
polypropyleneetherglycerol tris(4-aminobenzoate);
polypropyleneetherpentaerithritol tetrakis(4-aminobenzoate);
polyoxyethylene bis(4-aminobenzamide);
polyoxypropylene bis(4-aminobenzamide);
polyoxypropylene bis(3,5-diaminobenzamide); and
polyoxypropyleneetherglycerol tris(4-aminobenzamide); as revealed in U.S. Pat. No. 5,319,058, incorporated by reference hereinto in its entirety.

A suitable polyisocyanate is selected. A suitable polyisocyanate is one which is conventionally employed in the production of polyurethanes.

Examples of monomeric polyisocyanates useful herein include polyisocyanates and polyisothiocyanates which are PAPI-1(a polyaryl polyisocyanate as defined in U.S. Pat. No. 2,683,730), tolylene diisocyanate "TDI", triphenylmethane-4,4'4"-triisocyanate, benzene-1,3,5 -triisocyanate, toluene-2, 4,6-triisocyanate, diphenyl-2,4,4'-triisocyanate, , hexamethylene diisocyanate, xylylene diisocyanate, chlorophenylene diisocyanate, diphenylmethane-4,4'-diisocyanate, naphthalene-1,5-diisocyanate, xylene-alpha,alpha'-disothiocyanate, 3,3'-dimethyl-4,4'biphenylene diisocyanate, 3-3'dimethoxy-4,4'-biphenylene diisocyanate, 2', 3,3'-dimethyl-4,4'-biphenylene diisocynate, 5,5'-tetramethyl-4,4'biphenylene diisocyanate, 2,2', 5,5'-tetramethyl-4,4'biphenylene diisocyanate, 4,4'methylenebis (phenylisocyanate), 4,4'-sulfonylbis (phenylisocyanate), 4,4'-methylene di-orthotolylisocyanate, ethylene diisocyanate, ethylene diisothiocyanate, trimethylenediisocyanate and the like. Mixtures of any one or more of the above mentioned organic isothiocyanates or isocyanates may be used as desired.

Additionally, suitable are mixtures of TDI such as a mixture (80/20 by weight) of 2,4-toluene diisocyanate and 2,6 toluene diisocyanate or a mixture (65/35 by weight) of 2,4-toluene diisocyanate and 2,6-toluene diisocyanate; tetramethylene diisocyanate; hexamethylene diisocyanate; xylene diisocyanate; 1,5-napthylene diisocyanate; 1,4-phenylene diisocyanate; 4,4'-'diphenylmethane diisocyanate (MDI) (Upjohn's ISONATE® 125M); 4,4'4"-triphenylmethane triisocyanate; and 3,3'-dimethyl-4,4'-diphenylmethane diisocyanate. Aliphatic diisocyanates such as the $C_{36}$ aliphatic diisocyanate derived from the dimer of ricinoleic acid can be suitably employed and are commercially available, for example, as DDI-1410 (Henkel Corporation, Resin Division, Minneapolis, Minn.). The polyisocyanates hereof are known polyisocyanates in the field of polyurethane technology and can be employed singly or in admixture. Other examples of such polyisocyanates can be found, for example, in *The Development and Use of Polyurethane Products*, E. N. Doyle, McGraw-Hill Book Company, page 27 (1971), and *Polyurethane Handbook*, $2^{nd}$ Ed., Gunter Oertel Hauser, Gardner Press (1994).

Preferred polyisocyanates for employment in the process of the present invention are polyisocyanate materials in a liquid form at ambient temperatures e.g. a liquid MDI product as disclosed in U.S. Patent No. 3,394,164. These materials facilitate the production of polymeric products from normally liquid oligomeric aminobenzoic acid esters or amides and obviate the requirement of melting a solid polyisocyanate as a prerequisite to providing a suitable reaction mixture. Suitable liquid polyisocyanate materials are known and include, for example, polymeric MDI (4,4'-diphenylmethane diisocyanate) products obtained as by-products from the synthesis of MDI.

In the production of MDI by the condensation of aniline with formaldehyde and the conversation of amino to corresponding isocyanate groups, a content of the initially formed bis-adduct of aniline and formaldehyde reacts further with the reaction mixture to form polymeric aniline derivatives which are in turn converted to isocyanates. Typically, such polymeric derivatives will have a functionality of from about 4 to about 15, for example, about 10 isocyanate groups per molecule. Products containing such polymeric polyisocyanates in the form of a pot residue after removal of pure MDI by distillation can be utilized. Similarly, polyisocyanate products comprising such polymeric polyisocyanate species in admixture with pure MDI, i.e., the undistilled reaction mixture, can be employed. Polymeric MDI products can be employed herein to advantage and are commercially available under such trade designations as RURBINATE® M, RUBINATE® LF-168 and RUBINATE® LF-209 (available from Rubicon Chemicals Inc., Geisman, La.) and PaPI 27, PaPI 135, PaPI 580 and PaPI 901 (available from the Upjohn Company, Kalamazoo, Mich.).

Another liquid polyisocyanate material which can be employed where cross-linking is desirably introduced into the polymeric products hereof comprises an admixture of MDI and a tri-functional cycloaddition product of MDI. An admixture of MDI and a tri-functional cycloadduct having the following structure, where R is

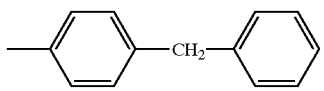

can be employed:

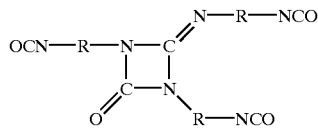

Such an admixture is available under the designation "Liquid MDI", Isonate® 2143L, (Dow Chemical, Midland, Mich.).

To reiterate, in addition to the preferred MDI, modified forms of monomeric MDI or MDI-containing resins, any suitable organic diisocyanate may be used in the process of this invention such as, for example, aliphatic diisocyanates, aromatic diisocyanates, alicyclic diisocyanates, and heterocyclic diisocyanates including such as, for example, ethylene diisocyanate, ethylidene diisocyanate, propylene diisocyanate, butylene diisocyanate, cyclopentylene-1,3-dissocyanate, cyclohexylene-1,4-diisocyanate, cyclohexylene-1,2-diisocyanate, 2,4-tolylene diisocyanate, 2,6-tolylene diisocyanate, 4,4'-diphenylmethane diisocyanate, 2,2-diphenylpropane-4,4'-diisocyanate, p-phenylene diisocyanate, m-phenylene diisocyanate, xylylene diisocyanate, 1,4-napthylene diisocyanate, 1,5-naphthylene diisocyanate, diphenyl-4,4'diisocyanate, azobenzene-4,4'-diisocyanate, diphenylsulfone-4,4'-diisocyanate, dichlorohexamethylene diisocyanate, tetramethylene diisocyanate, pentametylene diisocyanate, hexamethylene diisocyanate, 1-chloroboenzene-2,4-diisocyanate, furfurylidene diisocyanate, triphenyl methane triisocyanate and the like.

Other examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'dicyclohexyl-methane diisocyanate, 1,3- and 1,4-bis(isocyanatomethyl)-cyclohexane, bis-(4-isocyanato-3-methyl-cyclohexyl)-methane, α, α, α', α'-tetramethyl-1,3-1-isocyanato-1-methyl-4(3)-isocyanatomethyl cyclohexane, 2,4-, 1,3- and/or 1,4-phenylene diisocyanante, 2,4- and/or 2,6-toluylene diisocyanate, 2,4- and/or 4,4'-diphenyl-methane diisocyanate, 1,5-diisocyanato naphthalene and mixtures thereof. Aromatic polyisocyanates containing 3 or more isocyanate groups such as 4,4',4"-triphenylmethane diisocyanate.

In accordance with the present invention the polyisocyanate component can be in the form of an NCO prepolymer or a polyisocyanate adduct, more preferably a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight. The isocyanato-isocyanurates generally have an average NCO functionality of 3 to 3.5 and an NCO content of 5 to 30%, preferably 10 to 25% and most preferably 15 to 25% by weight.

Preferred polyisocyanate adducts are the polyisocyanates containing isocyanurate groups, biuret groups or mixtures of isocyanurate and allophanate groups.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (OH number).

With regard to the organic diisocyanes, the prepolymers and the polyisocyanate adducts, reference is made to U.S. Pat. No. 5,516,873, which is incorporated by reference hereinto in its entirety.

The first and second components are combined just prior to the application to a nail, claw or hoof in substantially equivalent proportions to form the liquid reaction solution. By "substantially equivalent" refers to the utilization, in general, of an amount of polyisocyanate component or reactant of about 0.9 to 1.2 equivalents per equivalent of the first component, i.e. the oligomeric aminobenzoic acid ester or amide, based upon the isocyanate groups and amino groups, respectively of the polyisocyanate and oligomeric amino benzoic acid ester or amide reactants. Preferably, from about 1.0 to about 1.15 equivalent of polyisocyanate material per equivalent of ologomeric aminobenzoic acid ester or amide is employed.

In practice, the reaction solution is applied to a nail, afflicted with onychomycosis, i.e. nail fungus, by any conventional topical means, e.g. brushing, swabbing, spraying, etc., until a liquid film or layer of a suitable thickness, is formed. The reaction mixture containing liquid film penetrates the nail, sufficient to a depth and the first and second components chemically react, typically after five to fifteen minutes, to polymerize to form a polyurea therapeutic coat on the treated nail. The cure time can be reduced by applying heat to the nail, e.g. with a heating lamp, minutes to affect the therapeutic polyurea coat. It has been found that such treatment of a nail having onychomycosis, i.e. a nail fungus, once per week for several weeks, leads and new nail growth. For severe cases the reaction solution can be applied once per day, typically, the application is carried out every second or third day.

In another embodiment, a stabilized reaction solution is utilized as a therapeutic polyurea composition. A first component is selected from the oligomeric amino benzoic acid ester or amide of formula I or an aromatic diamine derivative, which is combined with the polyisocyanate second component in a suitable stabilizing carrier to form a stabilized reaction solution destined to be used to treat onychomycosis.

A suitable aromatic diamine derivative includes (a) an aromatic diamine of the formula,

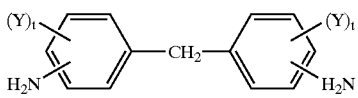

(I)

where each Y is independently from one another H, loweralkyl, loweralkoxy, halogen and $CF_3$, where the term "lower" means the group it is describing contains from 1 to 6 carbon atoms; where the term "alkyl" refers to a straight or branched chain hydrocarbon containing no unsaturation, e.g. methyl, ethyl, isopropyl, 2-butyl, neopentyl, n-hexyl, etc; where the term "alkoxy" has the formula loweralkyl-O—; and t is an integer of 1 to 4; some suitable diamines of the formula (I) include, 4,4'methylene bisaniline; 4,4'methylene bis(2-chloroaniline); 4,4'methylene bis(2,3-dichloroaniline) TCDAM); 4,4'methylene bis(2,5-dichloroaniline); 4,4'methylene bis(2-methylaniline); 4,4'methylene bis(2-ethylaniline); 4,4'methylene bis(2-isopropylaniline); 4,4'methylene bis(2,6-dimethylaniline); 4,4'methylene bis(2,6-diethylaniline); 4,4'methylene bis(2-ethyl-6-methylaniline); 4,4'methylene bis(2-chloro-6-methylaniline); 4,4'methylene bis(2-chloro-6-ethylaniline); 4,4'methylene bis(3-chloro-2,6-diethylaniline); 4,4'methylene bis(2-trifluoromethylaniline); 4,4'methylene bis(2-methyoxycarbonylaniline); and the like;
(b) a diphenyl ether derivative of the formula

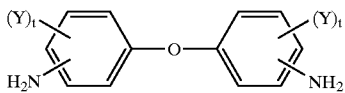

(2)

where Y and t are as previously defined; some suitable diamines of the formula (2) include 4,4'diaminodiphenyl ether; and 4,4'diamino-3,3'dichlorodiphenyl ether; (c) a diphenyl sulfone derivative of the formula

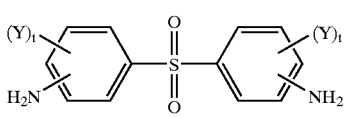

(3)

where Y and t are as previously defined; some suitable sulfone derivatives of formula (3) include, 4,4'-diaminodiphenyl sulfone; 4,4'-diamino-3,3'-dichlorodiphenyl sulfone; bis(4-aminophenoxyphenyl) sulfone; 1,2-bis(2-aminophenylthio)ethane; bis[2-(2-aminophenylthio)ethyl]terephthalate; and the like; (d), a diaminotoluene, such as 2,4-diaminotoluene; 2,6-diaminotoluene; 3,5-diethyl-2,4-diaminotoluene; 3,5-diethyl-2,6 diaminotoluene; 3,5-dimethylthio-2,4-diaminotoluene; 3,5-dimethylthio-2,6-diaminotoluene and the like; (e) a diaminodiphenyl-propane derivative of the formula

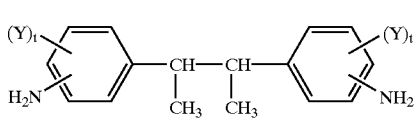

(4)

where Y and t are as previously defined; such as 2,2-bis(4-aminophenyl)propane; 2,2-bis(4-amino-3-methylphenyl)propane; 2,2-bis(4-amino-3-isopropylphenyl)propane; 2,2-bis(4-amino-3,5-dimethylphenyl)propane; 2,2-bis(4-amino-3,5-diethylphenyl)propane; 2,2-bis(4-amino-3,5-diisopropylphenyl)propane; 2,2-bis(4-amino-3-ethyl-5-methylphenyl)propane and the like; (f) an ester of an amino benzoic acid of the formula

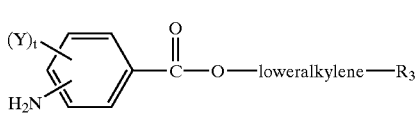

(5)

where the term "alkylene" refers to a bivalent radical of the lower branched or unbranched alkyl group it is derived from, having valence bonds from the terminal carbons thereof, e.g. ethyl (—$CH_2CH_2$—), propyl (—$CH_2CH_2CH_2$—), isopropyl ($CH_3CH$—$CH_3$), etc.; where $R_3$ H and.

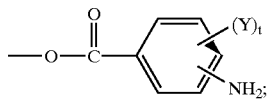

where Y and t are as previously defined; (g) 3,3'diaminobenzophenone; (h) m- or p-phenyl diamine; (i) m- or p-xylylenediamine; and (j) aromatic tetramine compounds such as 3,3',4,4'-tetraaminodiphenyl ether; 3,3',4,4'-tetraaminobiphenyl and the like; and so on. These aromatic polyamine compounds can be used either singly or as a combination of two kinds or more according to need and are disclosed in U.S. Pat. No. 5,319,058, incorporated hereinto by reference in its entirety.

The suitable stabilizing carrier is selected. A suitable stabilizing carrier is one which will completely dissolve the selected aminobenzoic acid ester or amide or the aromatic diamine derivative and the selected polyisocyanate when they are combined to form a stabilizing reaction solution but which will prevent the resultant polymeric reaction product, i.e. the polyurea, from solidifying or gelling out of the stabilized reaction solution. In other words, the stabilizing carrier either prevents the normally rapid reaction between the isocyanate group and the amino group or prevents the resultant reaction product, e.g. polyurea, from solidifying or gelling until such time as a portion of the stabilizing carrier or solvent is removed from the resultant solution, e.g., as by evaporation, thus permitting a greater time period in which to apply the resultant therapeutic polyurea composition to react with and penetrate the treated nail.

A suitable stabilizing carrier comprises a stabilizing solvent selected from (a) an aldehyde or ketone of the formula

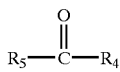 (6)

where $R_4$ and $R_5$ are independently of each other and are hydrogen and lower alkyl or $R_4$ and $R_5$ are joined to form a five or six membered ring; where the term "lower" is as previously defined; and where the term "alkyl" is as previously defined; (b) an ester having the formula

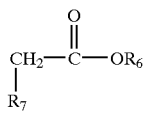 (7)

where $R_6$ and $R_7$ are loweralkyl (as previously defined) and $R_7$ additionally is H and loweralkoxy, where the term "lower" is as previously defined and the term "alkoxy" is as previously defined; (c) ortho, meta- or para-dimethylbenzene; (d) N-methylpyrrolidone; (e) Solvesso solvent, a petroleum hydrocarbon; (f) a lactone of the formula

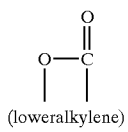 (8)

(loweralkylene)

where "lower" and "alkylene" is as previously defined; such as γ-butyrolactone; and a mixture of any of the oregoing solvents; combined with at least one polyol of the formula HO-loweralkylene-OH (9)

where "lower" and "alkylene" are as previously defined.

Some suitable aldehydes and ketones, for example, include acetone, methyl ethyl ketone, methylisobutylketone, N-methylcyclohexanone, benzaldehyde, acetaldehyde, propionaldehyde, butyraldehyde and isobutyraldehyde. Some suitable solvents of formula (b) include methyl acetate, ethyl acetate, butyl acetate, methoxy propyl acetate and methyl ether acetate. Some suitable polyols include, for example, polyglycols of the formula

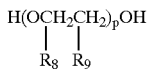 (10)

where p is an integer equal to 1 to 14, as for example when p is equal to 1 to 3, such compounds as ethylene glycol, propylene glycol, butylene glycols, such as 1,3-, 1,4-, and 2-3-butylene glycol, and alkylene glycols having 5 to 9 carbon atoms; when n is 4 or greater, polyglycols of an average molecular weight of about 600, such as polyethylene glycol 200, polyethylene glycol 400 and polyethylene glycol 600. It is to be understood that a mixture of the stabilizing solvents, e.g. aldehydes and ketones, can be employed, as well as a mixture of polyols, e.g., a mixture of ethylene glycol and propylene glycol.

The selected oligomeric aminobenzoic acid ester or amide or aromatic diamine derivative and the selected polyisocyanate components are added to the stabilizing carrier solution to form a stabilized reaction solution. Again, as with the reaction solution previously discussed, conventionally, these reaction components are combined in the stabilizing carrier in solution in substantially equivalent proportions, that is in amount of the polyisocyanate of about 0.9 to 1.2 equivalents per equivalent of the first component of oligomeric aminobenzoic ester or amide or aromatic diamine derivative, based upon the isocyanate groups and amino groups, respectively, of the polyisocyanate and oligomeric aminobenzoic acid ester or amide or diamine derivative reactants. Typically, from about 1.0 to about 1.15 equivalent of polyisocyanate material per equivalent of the first component e.g. oligomeric aminobenzoic acid ester or amide is employed.

Preferably, the primary reactants, e.g. the ester or amide (Formula I), and the polyisocyanate are combined in a volume ratio whereby the isocyanate is in excess to the ester or amide or diamine and is expressed in the following manner:

$$\frac{100}{0.95} \times \frac{1}{\text{Total Equivalent Weight of the first component e.g. the oligomeric ester or amide (grams/mole equivalent)}} \times \frac{4200}{\text{percent volume of the polyisocyanate second component,}}$$

which gives the parts of the polyisocyanate per 100 parts of the first reactant e.g. the oligomeric aminobenzoic acid ester or amide.

The amount of stabilizing carrier agent employed is one which is sufficient to dissolve the first reactant, e.g. the oligomeric aminobenzoic acid ester or amide reactant or diamine derivative reactant, and the polyisocyanate second reactant, and maintain the reaction product thereof, i.e., the polyurea, in solution without the precipitation out or gelling of the polyurea product. Typically, the amount of stabilizing carrier employed is about 10 to 80 volume percent of the total reaction solution. Typically the amount of the stabilizing solvent, e.g. aldehyde and/or ketone of formula (6), employed with at least one polyol of formula (9) is in the ratio of 10 to 80 parts of solvent to 1 part of polyol. The amount of stabilizing solvent, e.g., acetone, is adjusted depending upon the viscosity desired for specific application requirements, e.g. for maximum penetration and a desired coating thickness on the treated nail.

Polymerization additives of various types employed in the manufacture of polymeric products can desirably be employed in the stabilized reaction solution. For example, such polymerization agents as ultraviolet absorbers, fillers, plasticizers, etc., can be employed where desired.

Typically a flow and leveling agent polymerization additive is employed. Preferably such additive comprises a glycidyl ester of neo decanoic acid, of the formula

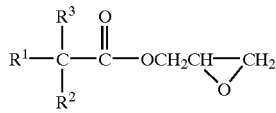

where the $R^1$, $R^2$, $R^3$ are independently of each other H and loweralkyl where the sum of each alkyl group of $R^1$, $R^2$, and $R^3$ does not exceed 8 carbon atoms. Other flow and leveling agents include the diglycidyl ether of 1,4-butane diol, the diglycidyl ether of neopentyl glycol, the poliglycidyl ether of aliphatic polyols, phenyl glycidyl ether, nonyl phenyl glycidyl ether, $C_9$–$C_{18}$ glycidyl ethers, polyglycidyl ether of castor oil, trimethyol ethane of triglycidyl ether and the ester forms of the aforementioned ethers. These ethers and esters are commercially available from the Shell Chemical Company and are designated as HELOXY products. The glycidyl neodecanoate is commercially available from Exxon Chemical Company and is known as GLYDEXX® N-10.

Specifically, GLYDEXX® N-10 ("N-10") is neodecanoic acid, oxiranyl methyl ester which is a reactive diluent, i.e. a substance which substitutes as a solvent but which is a non-volatile portion of the binder or curative due to its high boiling point of 255° F. and a vapor pressure of 0.11 mmHg at 68° F.

N-10 effects rapid uniform and leveling characteristics to a polymer coating.

Additionally, employed is an ultraviolet (UV) light absorber such as benzotriazoles, e.g. benzotriazoles revealed in U.S. Pat. Nos. 3,004,896 and 3,189,615. Such benzotriazoles are commercially available from Ciba Geigy as Tinuvin® products, such as Tinuvin® P, (2-(2H-benzotriazol-2yl))-4-methylphenol); Tinuvin® 1130, comprising about fifty-two weight percent of poly(oxy-1,2-ethanediyl), α-(3-(3-(2H-benzotriazol-2-yl)-5-(1,1-dimethylethyl)-4-hydroxyphenyl)-1-oxopropyl)-ω-hydroxy, of the formula,

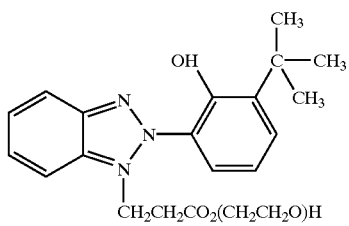

having an average molecular weight of 637, about thirty five weight percent of poly(oxy-1,2-ethanediyl), α-(3-(3-2H-benzotriazole-2-yl)-5-(1,1-dimethylethyl)-4-hydroxyphenyl)-1-oxopropyl-ω)-(3-(3-2H-benzotriazol-2-yl)-5-(1,1-diamethylethyl)-4-hydroxyphenyl)-1-oxopropyoxy), of the formula,

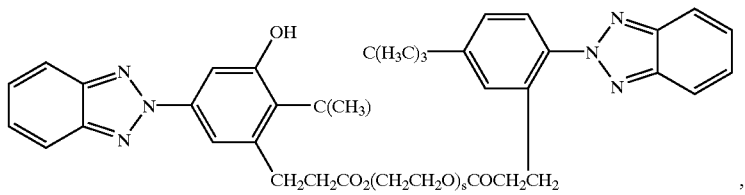

having an average molecular weight of 975, and the remainder (about thirteen weight percent of polyethylene glycol (300 molecular weight), which is used to functionalize the Tinuvin® 1130; Tinuvin® 292 and Tinuvin® 328, [2-(2'-hydroxyl-3,5'-di-tert-amylphenyl)benzotriazole].

Finally, an antioxidant may be employed. A preferred antioxidant is 3,5-di-tert-butyl-4-hydroxycinnamate, known as IRGANOX 1076.

A preferred UV stabilizer/antioxidant additive composition comprises about 70–75 weight percent of Tinuvin® 1130, 10–15 weight percent IRGANOX 1076 and 10–20 weight percent of Tinuvin® 328.

The concentration of the additives, e.g. uv stabilizer, antioxidant, leveling agent, etc. of the total formulation will be varied accordingly in a manner well known to those skilled in the art. Typically, where the reactants are VERSALINK® P-1000 and ISONATE® 2143L, the carrier solvent is acetone and the leveling agent GLYDDEX®T N-10 is employed ("FORMULATION"), the polyol component of the stabilizing carrier in the stabilized reaction solution and the FORMULATION is present in an amount which is in the ratio of the oligomeric aminobenzoic acid ester to the polyol of 5 to 2.66 to 1, preferably between 4.25 and 3.75 to 1, and, most preferably 4.0 to 1.

If a mixture of polyols is employed in the FORMULATION, e.g., ethylene glycol ("EG") and propylene glycol ("PPG"), each polyol preferably should be present in equal amounts.

Additionally, typically, for the FORMULATION, the ratio of N-10/2143L is equal to or less than the ratio of EG+PPG/2143L. The ratio range is typically 0.72 to 1.3, preferably 0.85 to 1.15, and most preferably 1.0 for N-10/2143L to EG+PPG/2143L.

Finally, for the FORMULATION, the ratio of EG+N-10/2143L to PPG+N-10/2143L is typically 1.

Another ratio which is considered with the FORMULATION is the ratio of EG/N-10 and PPG/N-10 which typically are equal to each other as well as equal to twice that of (EG+PPG)/2143L. Typically, the ratio of EG/N-10 to PPG/N-10 is 0.8 to 1.42, preferably 0.92 to 1.2 and most preferably 1.0.

The stabilized reaction solution can be stored in a sealed container without the reactants reacting until needed. As previously discussed, the stabilized reaction solution is applied to the affected nail by conventional topical means, to form a liquid film of a desired thickness. The stabilized reaction solution is treated, e.g. by heating, evaporation, etc., to remove at least a portion of the stabilizing carrier to form a solid cured polyurea material which has penetrated into the depth of the nail, and has formed the therapeutic polyurea coat thereon.

The fact that the stabilizing reaction solution can be applied without reaction spontaneously occurring, permits greater penetration of the stabilized reaction solution into the affected nail until removal of a portion of the stabilizing carrier is carried out. This is a great advantage in treating nails, e.g. hand or toe, claws or hoofs, of a patient in need thereof for a problem such as onychomycosis or nail fungus.

It is to be noted and stressed that the reaction solution and the stabilized reaction solution, described previously, and the blocked reaction solution to be hereafter described, have the property of chemically binding to skin proteins, and more generally to bodily ones, showing a real therapeutic action on the alteration of animal skin, particularly human skin. These reaction solutions and the resultant reaction products, e.g. polyurea, have the capacity of closely binding to the skin through either chemical or physical means, and possess elasticity very similar to that of skin, good abrasion resistance and impermeability to water.

The resultant oligomeric film when applied as a thin film, reacts with andemains bound to the nail, claw or hoof protecting the underlying derma while accelerating regeneration of skin and nail or claw or hoof.

In another embodiment for treating onychomycosis, a blocked reaction solution is employed as the therapeutic polyurea composition. In particular, the oligomeric polyamino benzoic acid ester or amide of formula I, is selected. Preferably, the compound of formula I is selected from the group consisting of polytetramethyleneglycol-di-p-aminobenzoates, polyethyleneglycol-di-p-aminobenzoates, and polypropyleneglycol-di-p-aminobenzoates.

The compound of formula I is reacted with an aromatic, heterocyclic, sterically hindered or long chain aldehyde to block at least one amino group of compound I.

Preferably, the aromatic aldehydes are represented by the formula (11):

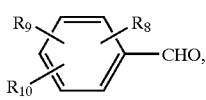

(II)

wherein $R_8$, $R_9$ and $R_{10}$ are hydrogen, halogen, $C_1$–$C_{20}$ alkyl, $C_1$–$C_{20}$ alkoxy, acyloxy, acylamino, or $C_1$–$C_{20}$ alkylthio.

Preferably, the said sterically hindered aldehydes are presented by the formula (12)

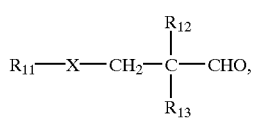

(12)

wherein $R_{11}$ is hydrogen or selected from the group consisting of aryl, substituted aryl, $C_1$–$C_{20}$ alkyl or aralkyl;

$R_{12}$ and $R_{13}$ are $C_1$–$C_6$ alkyl;

X is a covalent bond or selected from —O—, —CH$_2$—, —S—, —NHCOO—, —HNCONH—, —CONH—, —CONR$_{14}$— OR —COO—.

More preferably, the aldehydes are selected form the group consisting of benzaldehyde, anisaldehyde, furfural, ethoxybenzaldehyde, butoxybenzaldehyde, hexyloxybenzaldehyde, octyloxybenzaldehyde, decyloxybenzaldehyde, dodecyloxybenzaldehyde, hexadecyloxybenzaldehyde, ethylbenzaldehyde, isopropylbenzaldehyde and dimethylbenzaldehyde.

The blocked polyaminobenzoates or polyaminobenzamides of formula I of the present invention may be prepared by the following procedure:

The above described polyaminobenzoate or polyaminibenzamide of formula I is heated with an aldehyde to allow a dehydration reaction and the water generated by the reaction is distilled out azeotropically or absorbed by molecular sieves or reacted with a water sponger. These reactions can be carried out with or without a solvent. After completion of the reaction the solvent, if employed, is distilled off from the reaction mixture to obtain the desired aldimine.

The water sponger can be an organic mono- or polyisocyanate.

The resultant blocked polyaminobenzoate or polyaminobenzamide is then combined with the second component, i.e., the polyisocyanate, to form the blocked reaction composition or solution.

Preferably the polyisocyanate is carbodimide modified polyisocyanate, biuret modified polyisocyanate, isocyanurate modified polyisocyanate or urethane modified polyisocyanate.

Preferably the polyisocyanate is derived from a sterically hindered isocyanate.

More preferably the said polyisocyanate is represented by the formulat (13):

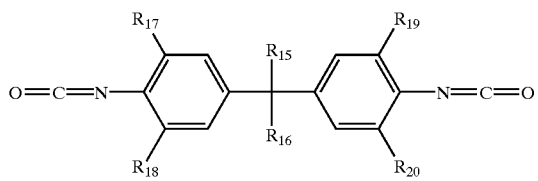

(13)

wherein $R_{15}$ and $R_{16}$ are hydrogen, $C_1$–$C_6$ alkyl or haloalkyl;

$R_{17}$, $R_{18}$, $R_{19}$, $R_{20}$ are hydrogen, halogen, $C_1$–$C_6$ alkyl or $C_1$–$C_6$ alkoxy.

Most preferably the polyisocyanate is an isocyanate-ended polyurethane/urea prepolymer. This prepolymer which has a plurality of iscocyanate groups and can be used for the invention is prepared by reacting the above organic polyisocyanate compound with a known polyol, known polyamine and other known compounds having two or more active hydrogens in a molecule. Free isocyanate groups are remained in the polyurethane prepolymer.

The resultant moisture curable polyurethane composition can be prepared by mixing the polyaldimine with the polyisocyanate and/or the polyurethane prepolymer containing the isocyante groups.

The ratio of the number of amino groups in the polyamine formed by the hydrolysis of the polyaldmine to the number of isocyanate groups contained in the above described polyisocyanate and/or the polyurethane prepolymer having the isocyanate groups is from 0.5 to 2.0, preferably from 0.7 to 1.5.

Further, a catylyst for curing can be incorporated into the blocked reaction composition as well as most solvents to control the viscosity. Suitable inert solvents include hexane, heptane, and octane; ethylacetate, butyl acetate, acetones, methyl ethylketone, methylisobutylketone cellosolve acetate, butyl cellosolve acetate, butiryl cellosolve acetate. These solvents can be used in the range of 50% by weight or less, preferably from 0 to 40% by weight of the composition.

Preferred curing acceleration catalysts include protic acids and phosphate esters. Preferably, the protic acids are carboxylic, sulfonic or phosphonic acids. The amount of these catalysts is in the range of preferably 0.05 to 5% by weight of the composition.

No particular restriction is imposed on the method of blending these components. Simple mixing or mixing by other known methods can be arbitrarily carried out.

When the additives have high moisture content, these additives must previously be dehydrated or addition of a dehydrating agent such as zeolite is required.

The resultant moisture curable blocked reaction composition or solution can be applied immediately to a nail needed to be treated or the solution can be stored in a sealed container for later usage. Upon application to the afflicted nail, as previously described, the liquid film, reacts with the moisture in the atmosphere to cure the polymer to form the therapeutic polyurea film or composition.

The above-described therapeutic polyurea compositions i.e. reaction solution, stabilized reaction solution and blocked reaction solution can be combined with pharmacologically acceptable additives, such as (1) plasticizers, e.g.

dialkylphthalates such as butylphthalate; hydroxy fatty acid oils such as castor oil; triglycerides, silicon oils; triactin, propylene glycol, and camphor; (2) film modifiers, which modify the hardness and/or flexibility of the resultant polyurea film, e.g. acrylic ester resins; cullulose derivatives, polyamide resins; (3) surfactants, e.g. polyethylene glycol-alkyl ethers; (4) penetration enhancers, e.g. azole, dimethyl sulfoxide, unsaturated fatty alcohols, propylene glycol, acetates, such as methyl acetate, butylacetate, ethylacetate, isobutyl acetate, isopropylacetate, propylacetate; (4) antioxidants, such as tocopherol; (5) nail softeners and avulsers, such as urea, sulfhydryl agents, sulfur based reducing agents, such as sodium sulfide; (6) for the reaction solution and blocked reaction solution, physcologically acceptable solvents. such as ethanol, isopropanol, acetone, ethyl acetate; (7) u.v. adsorbers, etc.

In a separate embodiment, the onychomycosis effective therapeutic polyurea composition, i.e. solutions, can be combined with an antifungal or antimycotic agent to form an onychomycosis treating composition. The components of the reaction solution, the stabilized reaction solution, the blocked reaction solution, or any mixture thereof are combined with the anti fungal agent in an effective amount thereof to treat nail fungus in a patient in need thereof.

Some suitable antifungal or antimycotic agents include, ciclopiroxolamine, ticonazole, econazole, oxiconazole, miconazole, tolnafate, naftifine hydrochloride, clotrimazole, griseofulvin, sulbentine, mometasonefuroate, terbinafine, ketoconazole, itraconazole, fluconazole, terconazole, saperconazole, amorolfine, oxiconazole. The selected antifungal or mixture thereof combined with the therapeutic polyurea solution in an amount which when the resultant onychomycosis treating composition is applied to a nail, the amount contained in the film penetrating and overcoating the nail will be effective in treating the nail fungus. For example, where griseofulvin is employed, the resultant composition will have from about 0.5 to about 10 percent be weight of this medicament to the total weight of the composition. Where mometasone furoate is employed, the concentration thereof will range from about 0.01 to one weight percent of the total composition.

It has surprisingly been found that when the therapeutic polyurea composition, selected from (a) the reaction solution, (b) the stabilized reaction solution, (c) the blocked reaction solution or composition, or (d) a mixture of any of the foregoing solutions, is applied to a health nail or a nail having onychomycosis, the nail resulting is (1) hardened, thereby alleviating a brittleness condition, and (2) water impermeable, thereby making it ideal for a nail polish or lacquer. Accordingly, a colored pigment or any additive utilized in the cosmetics industry for fabricating a cosmetic nail coating, or nail polish, can be incorporated into the therapeutic polyurea composition to form such a cosmetic nail coating or nail polish.

Typically, additives common in the cosmetics industry are employed with the therapeutic polyurea composition to form a cosmetic nail polish or lacquer. Such additives as plasticizers, colorants, pigments, perlescent agents, sedimentation retarders, sulfonamide resins, silicates, perfumes, wetting agents e.g. sodium dioctylsulfosuccinate, lanoline derivatives, sunscreen agents, e.g. 2-hydroxy-4-methoxybenzophenone, antibacterials with keratolytic and/or keratoplastic action e.g. aumonium sulfite, esters and salts of thioglucote acid, urea, allantoin, enzymes, salicylic acid, etc., may be employed in a customary fashion of the cosmetics industry to prepare the cosmetic nail polish or lacquer.

In a separate embodiment, the therapeutic polyurea composition can be employed to fabricate an artificial finger nail. Typically, a pigment utilized in nail fabrication is selected and combined with the therapeutic polyurea solutions to form an artificial nail composition. The pigment is provided in a concentration sufficient to provide the opacity and color of the finished nail. The pigment is added to the components of the therapeutic polyurea composition in a range of about 1.5–15% by weight of the total formulation. The exact amount of the pigment that is incorporated in the resultant artificial nail is determined by the nail technician. With too little pigment, the resultant nail does not have the opaque colored appearance of a nail covered with a conventional nail polish.

As previously indicated, the artificial nail composition may also contain such additives as antioxidants, calcium compounds to promote hardening of the natural nail, conventional solvent type plasticisers, such as phtalate esters, opacifiers or colorant extenders, such as titanium dioxide or alkyl polysiloxane and conventional dispersing agents for pigments and the like.

Lighter shades of color, such as red, can be formed by adding a relatively large amount of white opacifier, usually titanium dioxide. The titanium dioxide effectively dilutes the pigment to provide a lighter color.

Pearlized colors are provided by adding pearlescent or iridescent pigments in a relatively large amount, relative to the chosen colored pigment. Pearlescent pigments are available in a wide variety of colors from Mearl Corporation, New York, N.Y.

The use of pigments in the present invention is preferred over dyes for example, because pigments provide for a much more intense coloration, whereas dyes typically only provide for tinting or shading.

The artificial nail of this invention is made by removing any existing artificial nail, pushing back the cuticle, buffing the natural shine from the nail, gluing the tip overlays on the natural nail, clipping off the tip overlays, buffing the shine off the tip overlays, and buffing down the ridges of the overlays, spraying the nails and overlays with a nail cleanser, applying a primer, mixing the artificial nail composition of this invention and applying the resultant mixed artificial nail composition to the natural human nail and/or extensions.

The preferred technique is to create a ball of product on the end of a brush of the size used by artists and apply the ball to the tip of the substrate or tip overlay, brushing the material toward the tip. Additional balls of material are then applied inwardly toward the cuticle and brushed toward the tip. The ball of product applied near the cuticle is preferably thinned and less viscous. Surprisingly, the color of the nail near the tip is the same as the nail near the cuticle even though there is necessary more pigment near the tip.

The mixture is brushed over the natural nail and any substrate or tip overlay acting as an extender. The technician adds material until the nail has reached the desired thickness, length and overall shape. The nail cures to a colored velvety finish. After the nail cures, the technician files and shapes the nail in a conventional manner. By buffing with a conventional hand held buffer and some oil, the resultant nail is glossy and colored with the appearance of a conventional artificial nail covered with a conventional nail polish.

The curing mechanism of the present invention is specifically tailored to accommodate the use of pigment. Pigments reflect visible light, thus providing coloration. They are also capable of absorbing and reflecting ultaviolet radiation. Therefore, incorporating colored pigment into photocurable systems results in a dramatic lowering of the cure efficiency, significantly reducing the physical properties of a cured artificial nail. Dyes on the other hand, such as those disclosed in U.S. Pat. No. 4,058,442, are perfectly suited for UV cure systems, because dyes do not absorb UV light.

The artificial nail of this invention may be maintained or repaired in any conventional manner. When the natural nail first grows out to provide a noticeable gap between the nail and the cuticle, the technician or user buffs the ridge of the artificial nail near the cuticle and applies a coast of conventional nail polish. Because the underlying nail is colored, only one coat of polish is necessary, in contrast to conventional unpigmented artificial nails which require up to four coats of conventional nail polish.

Sooner or later, the nail grows out to an extent where a conventional artificial nail would be filled in. In this invention, there is preferably no filling in, however, 1 or 2 fill ins may be done. Upon removal, the nail technician removes the old nail, inspects for green spots or fungi infections and, if none, applies an new artificial nail of this invention. The full sculpt, material nail overlay or tip overlay procedure can be used depending on the preference of the nail technician.

With respect to the artificial nail of the invention, reference is made to U.S. Pat. No. 5,830,442, which is incorporated hereinto in its entirety.

I claim:

1. A method of treating onchomycosis of a nail of an animal in need thereof, which comprises
    (a) applying to the exterior surface of the nail a therapeutically effective amount of a therapeutic polyurea composition to form a liquid film thereon; and
    (b) curing said liquid film to form a therapeutic coat on at least said exterior surface.

2. The method as defined in claim 1 wherein said therapeutic polyurea composition is selected form the group consisting of (a) a reaction solution; (b) a stabilized reaction solution; (c) a blocked reaction solution; and (d) a mixture of any of the foregoing.

3. The method as defined in claim 2 wherein
    said reaction solution comprises a mixture of a first component comprising (a) an oligomeric aminobenzoic acid ester or amide of the formula,

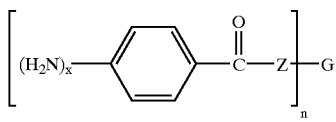

wherein n is an integer from 2 to 4, each x is one or two; each benzoyl nucleus is para-, meta or di-metaamino-substituted; each Z is —O— or —N—; and G is an n-valent radical obtained by removal of hydroxy groups or amino groups from an n-valent polyol or polyamine having a molecular weight of from about 400 to about 6,000; a suitable aromatic diamine or a mixture of the foregoing; combined with
    (b) a second component comprising a polyisocyanate;
    said stabilized reaction solution comprises said first and said second components and further a stabilizing carrier;
    said blocked reaction solution comprises said first component which has at least one of its aromatic amino groups blocked by reaction with an aldehyde prior to combining with said second component.

4. The method as defined in claim 3 wherein said therapeutic polyurea composition comprises said stabilized reaction solution and wherein said stabilizing carrier comprises a stabilizing solvent and a polyol.

5. The method as defined in claim 4 wherein said stabilizing solvent is selected from the group of (a') an aldehyde or kenote of the formula

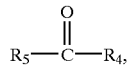

where $R_4$ and $R_5$ are independently of each other hydrogen and lower alkyl or $R_4$ and $R_5$ are joined to form a five or six-membered ring, (b') an ester having the formula,

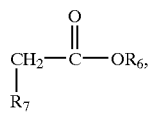

where $R_6$ and $R_7$ are independently loweralkyl and $R_7$ is additionally H and loweralkoxy, (c') ortho-, meta- or para-dimethyl benzene, (d') N-methyl pyrrolidone, (e') Solvesso solvent; (f') a petroleum hydrocarbon; (g') a lactone of the formula

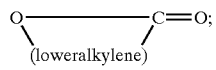

and (h') a mixture of any of the foregoing.

6. The method as defined in claim 5 wherein said stabilizing solvent is acetone.

7. The method as defined in claim 5 wherein said ester (b') comprises an acetate selected from the group consisting of methylacetate, ethylacetate, butylacetate, methoxypropyl acetate or a mixture of any of the foregoing acetates.

8. The method as defined in claim 4 wherein said polyol is one having the formula

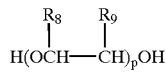

where p is an integer of 1 to 14 and $R_8$ and $R_9$ are independently of each other H and lower alkyl.

9. The method as defined in claim 8 wherein said polyol is one where p is equal to 1 to 3.

10. The method as defined in claim 9 wherein said polyol is one selected from the group consisting of ethylene glycol, propylene glycol, 1-3-butylene glycol, 1-4-butylene glycol, 2-3-butylene glycol and a mixture of any of the foregoing glycols.

11. The method as defined in claim 10 wherein said stabilizing solvent comprises acetone and said polyol comprises a mixture of ethylene glycol and propylene glycol.

12. The method as defined in claim 11 wherein said oligomeric amino benzoic acid amide has the formula

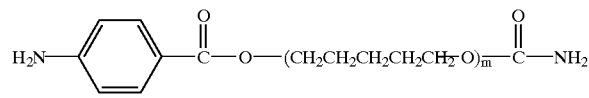

where m is an integer of 13 to 14, with a molecular weight of 1238.

13. The method as defined in claim 3, wherein said therapeutic polyurea composition comprises said blocked reaction solution, wherein said first component is selected from the group consisting of a polytretramethyleneglycol-di-p-amino-benzoate, a polyethyleneglycol-di-p-aminobenzoate and a polypropyleneglycol-di-p-amino benzoate; and wherein said aldehyde is selected from the group consisting of aromatic, heterocyclic, sterically hindered and long chain aldehydes.

14. The method as defined in claim 13, wherein said aldehyde has the formula,

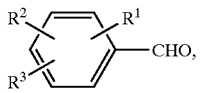

where $R^1$, $R^2$ and $R^3$ are independently of each other, hydrogen, halogen, $C_1$–$C_{20}$ alkyl, $C_1$–$C_{20}$ alkoxy, acyloxy, acylamino or $C_1$–$C_{20}$ alkylthio.

15. The method as defined in claim 13, wherein said aldehyde has the formula,

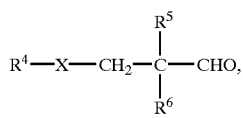

where $R^4$ is aryl, substituted aryl, $C_1$–$C_{20}$ alkyl, aralkyl, hydrogen; $R^5$ and $R^6$ are $C_1$–$C_6$ alkyl; X is a covalent bond or is selected from —O—, —CH$_2$—, —S—, —NHCOO—, —NHCONH—, —CONH—, —CONR$^5$ and —COO—.

16. The method as defined in claim 13 wherein said aldehyde is selected from the group consisting of benzaldehyde, anisaldehyde, furfuryl, ethoxybenzaldehyde, butoxybenzaldehyde, hexyl oxybenzaldehyde, octyloxybenzaldehyde, decyloxybenzaldehyde, isopropylbenzaldehyde and dimethylbenzaldehyde.

17. The method as defined in claim 13 wherein said second component has the formula,

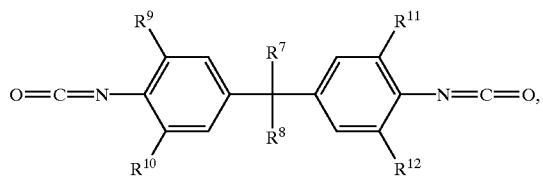

where $R^7$ and $R^8$ are each independent of the other hydrogen, $C_1$–$C_6$ alkyl, haloalkyl; $R^9$, $R^{10}$, $R^{10}$, $R^{11}$, $R^{12}$ are each independent of one another, hydrogen, halogen $C_1$–$C_6$ alkyl, $C_1$–$C_6$ alkoxy.

18. The method as defined in claim 1 wherein said composition additionally comprises an antimycotic or antifungal agent present in a concentration which provides a therapeutically effective amount in said therapeutic coat.

19. A composition for treating onychomycosis which comprises:
(a) a therapeutic polyurea composition; and
(b) an antimycotic agent present in a therapeutically effective amount added to said polyurea composition.

20. An antimycotic composition which comprises,
(a) a therapeutic polyurea composition which is selected from the group consisting of (a') a reaction solution; (b') a stabilized reaction solution; (c') a blocked reaction solution; and (d') a mixture of any of the foregoing; and (b) an antimycotic agent present in a therapeutically effective amount added to said polyurea composition.

21. The composition as defined in claim 20 wherein said reaction solution comprises a mixture of a first component comprising (a) an oligomeric aminobenzoic acid ester or amide of the formula,

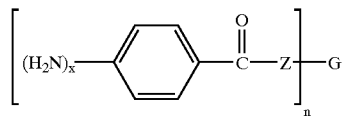

wherein n is an integer from 2 to 4, each x is one or two; each benzoyl nucleus is para-, meta or di-metaamino-substituted; each Z is —O— or —N—; and G is an n-valent radical obtained by removal of hydroxy groups or amino groups from an n-valent polyol or polyamine having a molecular weight of from about 400 to about 6,000; a suitable aromatic diamine or a mixture of the foregoing; combined with
(b) a second component comprising a polyisocyanate;
said stabilized reaction solution comprises said first and said second components and further a stabilizing carrier;
said blocked reaction solution comprises said first component which has at least one of its aromatic amino groups blocked by reaction with an aldehyde prior to combining with said second component.

22. The composition as defined in claim 21 wherein said therapeutic polyurea composition comprises said stabilized reaction solution and wherein said stabilizing carrier comprises a stabilizing solvent and a polyol.

23. The composition as defined in claim 22 wherein wherein said stabilizing solvent is selected from the group of (a') an aldehyde or ketone of the formula

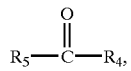

where $R_4$ and $R_5$ are independently of each other hydrogen and lower alkyl; or $R_4$ and $R_5$ are joined to form a five or six-membered ring, (b') an ester having the formula,

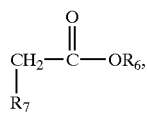

where $R_6$ and $R_7$ are independently loweralkyl and $R_7$ is additionally H and loweralkoxy, (c') ortho-, meta- or para-dimethyl benzene, (d') N-methyl pyrrolidone, (e') Solvesso solvent; (f') a petroleum hydrocarbon; (g') a lactone of the formula

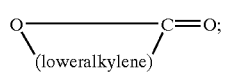

and (h') a mixture of any of the foregoing.

24. The composition as defined in claim 23 wherein said stabilizing solvent is acetone.

25. The composition as defined in claim 23 wherein said ester (b') comprises an acetate selected from the group consisting of methylacetate, ethylacetate, butylacetate, methoxypropyl acetate or a mixture of any of the foregoing acetates.

26. The composition as defined in claim 23 wherein said polyol is one having the formula

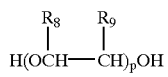

where p is an integer of 1 to 14 and $R_8$ and $R_9$ are independently of each other H and lower alkyl.

27. The composition as defined in claim 26 wherein said polyol is one where p is equal to 1 to 3.

28. The composition as defined in claim 27 wherein said polyol is one selected from the group consisting of ethylene glycol, propylene glycol, 1-3-butylene glycol, 1-4-butylene glycol, 2-3-butylene glycol and a mixture of any of the foregoing glycols.

29. The composition as defined in claim 28 wherein said stabilizing solvent comprises acetone and said polyol comprises a mixture of ethylene glycol and propylene glycol.

30. The composition as defined in claim 28 wherein said oligomeric amino benzoic acid amide has the formula

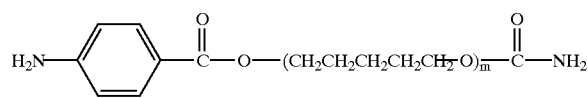

where m is an integer of 13 to 14, with a molecular weight of 1238.

31. The composition as defined in claim 19 wherein said antifungal agent is selected from the group consisting of ciclopiroxolamine, ticonazole, econazole, oxiconazole, miconazole, tolnafate, naftifine hydrochloride, clotrimazole, griseofulvin, sulbentine, mometasonefuroate, terbinafine, ketoconazole, itraconazole, fluconazole, terconazole, saperconazole, amorolfine, oxiconazole.

32. The composition as defined in claim 21 wherein said therapeutic polyurea composition comprises said blocked reaction solution, wherein said first component is selected from the group consisting of a polytretramethyleneglycol-di-p-amino-benzoate, a polyethyleneglycol-di-p-aminobenzoate and a polypropyleneglycol-di-p-amino benzoate; and wherein said aldehyde is selected from the group consisting of aromatic, heterocyclic, sterically hindered and long chain aldehydes.

33. The composition as defined in claim 32 wherein said aldehyde has the formula,

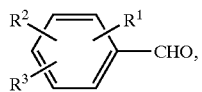

where $R^1$, $R^2$ and $R^3$ are independently of each other, hydrogen, halogen, $C_1$–$C_{20}$ alkyl, $C_1$–$C_{20}$ alkoxy, acyloxy, acylamino or $C_1$–$C_{20}$ alkylthio.

34. The composition as defined in claim 32 wherein said aldehyde has the formula,

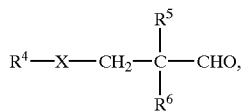

where $R^4$ is aryl, substituted aryl, $C_1$–$C_{20}$ alkyl, aralkyl, hydrogen $R^5$ and $R^6$ are $C_1$–$C_6$ alkyl; X is a covalent bond or is selected from —O—, —CH$_2$—, —S—, —NHCOO—, —NHCONH—, —CONH—, —CONR$^5$ and —COO—.

35. The composition as defined in claim 32 wherein said aldehyde is selected from the group consisting of benzaldehyde, anisaldehyde, furfuryl, ethoxybenzaldehyde, butoxybenzaldehyde, hexyl oxybenzaldehyde, octyloxybenzaldehyde, decylocybenzaldehyde, isopropylbenzaldehyde and dimethylbenzaldehyde.

36. The composition as defined in claim 32 wherein said second component has the formula,

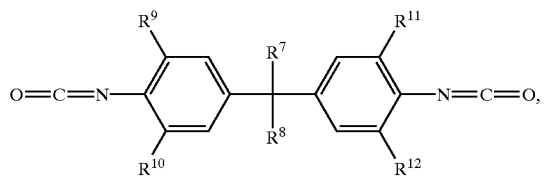

where $R^7$ and $R^8$ are each independent of the other hydrogen, $C_1$–$C_6$ alkyl, haloalkyl; $R^9$, $R^{10}$, $R^{11}$, $R^{12}$ are each independent of one another, hydrogen, halogen $C_1$–$C_6$ alkyl, $C_1$–$C_6$ alkoxy.

37. A therapeutic lacquer or polish for treating a nail, claw or hoof of an animal in need of therapeutic treatment, which comprises, (a) a therapeutic polyurea composition; and (b) at least one antimycotically active substance.

38. A method of therapeutically treating a nail, claw or hoof of an animal in need thereof which comprises applying the therapeutic lacquer or polish of claim 37 to the top surface of the nail, claw, or hoof.

39. A method for producing a self-curing, dermatologically acceptable pigmented artificial nail composition, applied to a natural nail or nail extension, comprising, combining a therapeutic polyurea composition with a pigment selected from the group consisting of lead chromate pigments, organic pigments, cadmium based pigments, pearlescent pigments and a mixture of any of the foregoing pigments;

wherein said pigmented artificial nail composition hardens to form an evenly-colored, glossy, apaque artificial nail, wherein said pigment is dispersed in said nail composition to provide a finished nail product.

40. A self-curing, dermatologically acceptable composition applied to a natural nail or extension as a coating that hardens to form an evenly colored, glossy, opaque, artificial nail, comprising, (a) a composition selected from the group consisting of a reaction solution, a stabilized reaction solution, a blocked reaction solution and a mixture of any of the foregoing solutions, combined with (b) a pigment selected from the group consisting of lead chromate pigments, organic pigments, cadmium based pigments, pearlescent pigments and a mixture of any of the foregoing pigments.

41. The composition as defined in claim 20 wherein said antimycotic agent is selected from the group consisting of econazole, oxiconazole, miconazole, tolnafate, naftifine hydrochloride, clortrimazole, griseofulvin, sulbentine, mometasone fuorate, terbinafine, ketoconazole, itraconazole, fluconazole, terconazole, saperconazole, amorolfine, oxiconazole and any mixture of the foregoing agents.

* * * * *

UNITED STATES PATENT AND TRADEMARK OFFICE
CERTIFICATE OF CORRECTION

PATENT NO. : 6,403,063 B1
DATED : June 11, 2002
INVENTOR(S) : Kenneth I. Sawyer

It is certified that error appears in the above-identified patent and that said Letters Patent is hereby corrected as shown below:

<u>Column 28,</u>
Line 5, delete "kenote" and substitute therefor -- ketone --.

Signed and Sealed this

Sixth Day of August, 2002

*Attest:*

JAMES E. ROGAN
*Attesting Officer*     *Director of the United States Patent and Trademark Office*